(12) United States Patent
Kale et al.

(10) Patent No.: US 10,165,985 B2
(45) Date of Patent: Jan. 1, 2019

(54) SYSTEM AND METHOD OF EXTRACTION OF THE HEART VALVE SIGNALS

(71) Applicant: AventuSoft, LLC, Boca Raton, FL (US)

(72) Inventors: Kaustubh Kale, Royal Palm Beach, FL (US); Luis Gonzalo Sanchez Giraldo, Miami, FL (US)

(73) Assignee: AVENTUSOFT LLC, Boca Raton, FL (US)

( * ) Notice: Subject to any disclaimer, the term of this patent is extended or adjusted under 35 U.S.C. 154(b) by 65 days.

(21) Appl. No.: 15/397,040

(22) Filed: Jan. 3, 2017

(65) Prior Publication Data

US 2017/0188869 A1    Jul. 6, 2017

Related U.S. Application Data

(60) Provisional application No. 62/274,763, filed on Jan. 4, 2016, provisional application No. 62/274,761, filed
(Continued)

(51) Int. Cl.
*A61B 5/00* (2006.01)
*A61B 5/0404* (2006.01)
(Continued)

(52) U.S. Cl.
CPC .......... *A61B 5/7282* (2013.01); *A61B 5/0006* (2013.01); *A61B 5/0008* (2013.01); *A61B 5/0022* (2013.01); *A61B 5/0205* (2013.01); *A61B 5/02028* (2013.01); *A61B 5/02444* (2013.01); *A61B 5/0404* (2013.01);
(Continued)

(58) Field of Classification Search
CPC ......... A61B 5/025; A61B 5/0205; A61B 5/72; A61B 5/7264; A61B 5/7282; A61B 5/02
See application file for complete search history.

(56) References Cited

U.S. PATENT DOCUMENTS 7,096,061 B2   8/2006   Arad
7,174,203 B2   2/2007   Arand et al.
(Continued)

OTHER PUBLICATIONS

Capan; Bernstein,et al.; Measurement of Ejection Fraction by Bioimpedeance . . . , Critical Care Med.; Apr. 1987, vol. 15, Issue 4, p. 402.
(Continued)

*Primary Examiner* — Scott M. Getzow
(74) *Attorney, Agent, or Firm* — Pablo Meles (57) ABSTRACT

A system for monitoring and diagnosing heart conditions includes a sensor array with accelerometers, an electrocardiogram sensor, and a system to capture and process the composite heart signals. The system performs source separation to extract information contained in cardio pulmonic vibrations. The system can use machine learning, auditory scene analysis, spare coding, determined Models, Principal Component Analysis (PCA), Independent Component Analysis ICA, Singular Value Decomposition (SVD), Binwise Clustering and Permutation posterior probability alignment, Undetermined Models, Sparseness condition, Dictionary learning, Convolutive models, K-SVD Matching Pursuit, Non-negative matrix factorization and Deep Belief Networks (Restricted Boltzmann Machine) approaches to the source separation problem. Other embodiments are disclosed.

20 Claims, 8 Drawing Sheets

Related U.S. Application Data on Jan. 4, 2016, provisional application No. 62/274,765, filed on Jan. 4, 2016, provisional application No. 62/274,766, filed on Jan. 4, 2016, provisional application No. 62/274,770, filed on Jan. 4, 2016.

(51) Int. Cl.

| | | |
|---|---|---|
| A61B 5/0456 | (2006.01) | |
| A61B 5/0205 | (2006.01) | |
| A61B 5/0468 | (2006.01) | |
| A61B 5/024 | (2006.01) | |
| A61B 5/04 | (2006.01) | |
| A61B 5/0432 | (2006.01) | |
| A61B 5/11 | (2006.01) | |
| A61B 5/02 | (2006.01) | |
| G06F 19/00 | (2018.01) | |
| G16H 40/67 | (2018.01) | |
| A61B 5/08 | (2006.01) | |

(52) U.S. Cl.
CPC ...... *A61B 5/04014* (2013.01); *A61B 5/04017* (2013.01); *A61B 5/0456* (2013.01); *A61B 5/0468* (2013.01); *A61B 5/04325* (2013.01); *A61B 5/1102* (2013.01); *A61B 5/6801* (2013.01); *A61B 5/6802* (2013.01); *A61B 5/6831* (2013.01); *A61B 5/6833* (2013.01); *A61B 5/7214* (2013.01); *A61B 5/7225* (2013.01); *G06F 19/00* (2013.01); *G16H 40/67* (2018.01); *A61B 5/024* (2013.01); *A61B 5/02055* (2013.01); *A61B 5/0816* (2013.01); *A61B 2562/0204* (2013.01); *A61B 2562/0219* (2013.01); *A61B 2562/06* (2013.01)

(56) References Cited

U.S. PATENT DOCUMENTS

| | | | |
|---|---|---|---|
| 7,351,207 | B2 | 4/2008 | Priemer |
| 8,105,241 | B2 | 1/2012 | Nelson et al. |
| 8,131,354 | B2 | 3/2012 | Arad |
| 8,251,911 | B2 | 8/2012 | MacQuarrie et al. |
| 8,255,042 | B2 | 8/2012 | MacQuarrie et al. |
| 8,290,577 | B2 | 10/2012 | Brooks et al. |
| 8,475,396 | B2 | 7/2013 | Jones et al. |
| 8,614,630 | B2 | 12/2013 | Narasimhan et al. |
| 8,688,202 | B2 | 4/2014 | Brockway et al. |
| 8,694,089 | B2 | 4/2014 | Arad |
| 8,715,206 | B2 | 5/2014 | Telfort et al. |
| 8,764,653 | B2 | 7/2014 | Kaminska et al. |
| 8,790,259 | B2 | 7/2014 | Katra et al. |
| 8,823,490 | B2 | 9/2014 | Libbus et al. |
| 8,868,175 | B2 | 10/2014 | Arad |
| 8,898,369 | B1 | 11/2014 | Yang |
| 9,035,794 | B2 | 5/2015 | Narasimhan et al. |
| 9,247,004 | B2 | 1/2016 | Azimi |
| 9,307,908 | B2 | 4/2016 | Chan et al. |
| 9,370,335 | B2 | 6/2016 | Al-Ali et al. |
| 9,445,719 | B2 | 9/2016 | Libbus et al. |
| 9,462,994 | B2 | 10/2016 | Rogers et al. |
| 2004/0006279 | A1 | 1/2004 | Arad |
| 2006/0095085 | A1 | 5/2006 | Marcus et al. |
| 2007/0219059 | A1 | 9/2007 | Schwartz et al. |
| 2011/0263994 | A1 | 10/2011 | Burns et al. |
| 2012/0209131 | A1 | 8/2012 | Jones et al. |
| 2013/0109989 | A1 | 5/2013 | Busse et al. |
| 2013/0245487 | A1 | 9/2013 | Aga |
| 2013/0281875 | A1 | 10/2013 | Narasimhan et al. |
| 2014/0019080 | A1 | 1/2014 | Chan et al. |
| 2014/0066795 | A1 | 3/2014 | Ferdosi et al. |
| 2014/0073982 | A1 | 3/2014 | Yang et al. |
| 2014/0200474 | A1 | 7/2014 | Selvaraj et al. |
| 2014/0275932 | A1 | 9/2014 | Zadig |
| 2014/0276127 | A1 | 9/2014 | Ferdosi et al. |
| 2015/0020571 | A1 | 1/2015 | Chan et al. |
| 2015/0038856 | A1 | 2/2015 | Houlton et al. |
| 2015/0045628 | A1 | 2/2015 | Moghadam et al. |
| 2015/0065894 | A1 | 3/2015 | Airaksinen et al. |
| 2015/0164410 | A1 | 6/2015 | Selvaraj et al. |
| 2015/0164411 | A1 | 6/2015 | Selvaraj et al. |

OTHER PUBLICATIONS

W. Chan M. Woldeyohannes et al.; Haemobdynamic and structural correlates . . . ; BMJ Open 2013;3:e002660.
C.L. Garrard, Jr et al.; The Relationship of Alterations in Systolic . . . : Circulation. 1970; vol. 42; pp. 455-462; Amer. Heart Association.
S. Toggweiler et al: Monitoring anthracycline chemotherapy patients; 2013; Clin. Cariol.; vol. 36, Issue 4, pp. 201-206.
S. Wang et al: Rapid Bedside Identification of high-rick population; International J. of Cariolody; Jan. 24, 2013; vol. 168, pp. 1881-1886.

SYSTEM AND METHOD OF EXTRACTION OF THE HEART VALVE SIGNALS

CROSS REFERENCE TO RELATED APPLICATIONS

This Application claims the priority benefit of Provisional Application Nos. 62/274,763, 62/274,761, 62/274,765, 62/274,766, and 62/274,770, each of which were filed on Jan. 4, 2016, the entire disclosure of each which are incorporated herein by reference.

FIELD

The embodiments herein relate generally to cardiac health monitoring and more particularly to analysis software combined with transducers to capture multichannel vibration signals along with an electrocardiogram signal for the measurement of heart functions.

BACKGROUND

Heart disease is the leading cause of death accounting for more than one-third (33.6%) of all U.S. deaths. Overall cardiac health can be significantly improved by proper triage. Low invasive and non-invasive ultrasound techniques (e.g. echocardiogram) are standard procedures, but the requirement of expensive devices and skilled operators limit their applicability. The following are the various types of heart disease that can be diagnosed and treated using the separated signal, namely, Coronary artery disease, Heart murmurs and valve abnormalities, Heart failure, Heart rhythm abnormalities (arrhythmias), Vascular disease, congenital heart disease, and Risk factor modification. A physician can work with patients to perform a comprehensive evaluation and design a personalized plan of care aimed at keeping them healthy.

The cardio pulmonary system which consists of the respiratory components, snoring components, and cardiac components, creates vibrations during each cardiac cycle. The vibrations are the result of the lung sounds, heart sounds, acceleration and deceleration of blood due to abrupt mechanical opening and closing of the valves during the cardiac cycle.

SUMMARY

The exemplary embodiments herein provide a method and system based on a technique for source separating the cardiopulmonary signals, to extract information contained from the cardiac vibration objects. In some embodiments, machine learning, auditory scene analysis, spare coding, determined Models, Principal Component Analysis (PCA), Independent Component Analysis ICA, Singular Value Decomposition (SVD), Bin-wise Clustering and Permutation posterior probability alignment, Undetermined Models, Sparseness condition, Dictionary learning, Convolutive models, K-SVD Matching Pursuit, Non-negative matrix factorization or Deep Belief Networks (Restricted Boltzmann Machine) are used as approaches to the source separation problem. Data is obtained using a tri-axial accelerometer or multiple tri-axial accelerometers placed on different points of a torso. Further note that the techniques and methods herein are not limited to acoustic, electrical or vibrational data as might be used in some stethoscopes, but can also be applied to other forms of monitoring such as echo imaging or sonograms, magnetic resonance imaging (MRI), computed tomography (CT) scanning, positron emission tomography (PET) scanning, and monitoring using various forms of catheterization. The techniques and methods herein are primarily applicable to monitoring of heart valve events, but can be alternatively applied to other types of involuntary biological signaling emanating from the brain, intrauterine, pre-natal contractions, or elsewhere within both humans and other species.

Examples of cardiac vibration objects are the first sound, the second sound, the third sound, the fourth sound, ejection sounds, opening sounds, murmurs, heart wall motions, coronary artery sounds, and valve sounds of the Mitral valve opening and closing, Aortic valve opening and closing, Pulmonary valve opening and closing, Tricuspid valve opening and closing. Examples of the pulmonary vibration objects are the respiratory lung sounds, breathing sounds, tracheobronchial sounds, vesicular sounds, Broncho vesicular sounds, snoring sounds. A portion of the energy produced by these vibrations lies in the infra-sound range, which falls in the inaudible and low sensitivity human hearing range. A portion of the energy produced by these vibrations falls in the audible hearing range. For example, the vibration objects from the Mitral, Tricuspid, Aortic, and Pulmonary valve openings fall in a lower range of vibrations such as 0 to 60 Hertz, whereas vibration objects from the Mitral, Tricuspid, Aortic, and Pulmonary valve closings fall in a higher range of vibrations such as 50 to 150 Hertz. Accelerometer transducers placed on the chest capture these vibrations from both these ranges.

Source separation analysis in accordance with the methods described herein extract individual vibration objects from the composite vibration signal captured on the surface. The individual vibration signals are identified to be from the mitral valve, aortic valve, tricuspid valve, the pulmonary valve, coronary artery, murmurs, third sound, fourth sound, respiratory sound, breathing, and snoring during individual heart beats. The identified signals are marked to indicate their start with respect to the start of the electrocardiogram or EKG.

DETAILED DESCRIPTION

The exemplary embodiments may be further understood with reference to the following description and the appended drawings, wherein like elements are referred to with the same reference numerals. The exemplary embodiments describe a system and method of source separation on the composite vibrations captured on the chest wall to extract the individual cardiopulmonary signals. Specifically, psychoacoustics are considered in separating cardiac vibration signals captured through the transducers. The system, the psychoacoustics, and a related method will be discussed in further detail below.

The embodiments can include different source separation techniques specifically used for extracting individual cardiopulmonary signals for application in a non-linear time variant system, such as, Determined Models, Principal Component Analysis (PCA), Independent Component Analysis ICA, Singular Value Decomposition (SVD), Bin-wise Clustering and Permutation posterior probability Alignment, Undetermined Models, Sparseness condition, Dictionary learning, Convolutive models, K-SVD Matching Pursuit, Non-negative matrix factorization and Deep Belief Networks (Restricted Boltzmann Machine).

The exemplary embodiments provide a novel approach for small, portable, robust, fast and configurable source separation based software with transducer hardware 103, 203. The use of the vibration signal pattern and novel psychoacoustics help bypass conventional issues faced by linear time invariant systems. The following are the various types of heart disease that can be diagnosed and treated using the separated signal, namely, Coronary artery disease, Heart murmurs and valve abnormalities, Heart failure, Heart rhythm abnormalities (arrhythmias), Vascular disease, congenital heart disease, and Risk factor modification. A physician can work with patients to perform a comprehensive evaluation and design a personalized plan of care aimed at keeping them healthy. The two major audible heart sounds in a normal cardiac cycle are the first and second heart sound, S1 and S2. S1 occurs at the onset of the ventricular contraction during the closure of the AV-valves. It contains a series of low-frequency vibrations, and is usually the longest and loudest heart sound. The audible sub-components of S1 are those associated with the closure of each of the two AV-valves. S2 is heard at the end of the ventricular systole, during the closure of the semilunar valves. Typically, its frequency is higher than S1, and its duration is shorter. It has aortic and pulmonary sub-components. A third low-frequency sound (S3, ventricular gallop) may be heard at the beginning of the diastole, during the rapid filling of the ventricles. A fourth heart sound (S4, atrial gallop) may be heard in late diastole during atrial contraction. Opening snaps of the mitral valve or ejection sound of the blood in the aorta may be heard in case of valve disease (stenosis, regurgitation). Murmurs are high-frequency, noise-like sounds that are heard between the two major heart sounds during systole or diastole. They can be innocent, but can also indicate certain cardiovascular defects. Fourth heart sound, abnormal left atrial filling waves, and third heart sounds are commonly found in patients with coronary artery disease, and left ventricular dysfunction. Extensive correlations of these clinical findings with hemodynamic have been demonstrated, providing the importance of extracting these signals from the composite signals for automated and remote monitoring and diagnosis. The third heart sound is a low frequency sound coinciding with the rapid filling phase of ventricular diastole. It is recorded 0.10 to 0.20 sec after the aortic component of the second sound and often corresponds to a rapid filling wave. The major vibrations of the fourth heart sound usually occur 0.12 to 0.17 sec after the onset of the P wave of the electrocardiogram. These vibrations usually precede the onset of the QRS complex, except in instances of short P-R intervals. Unless the P-R interval is prolonged, the fourth heart sound is normally inaudible, although some small, insignificant vibrations can be recorded at low frequency ranges. Significant (abnormal) vibrations have greater amplitude and pitch, and constitute the clinically audible fourth heart sound. They are readily recorded, even at medium frequency ranges. The signals of the biomechanical system show a high clinical relevance when auscultated on the chest. The heart and lung sounds are applied to the diagnosis of cardiac and respiratory disturbances, whereas the snoring sounds have been acknowledged as important symptoms of the airway obstruction. The innovation here provides extraction of all three types of body sounds from the composite vibration captured at the skin. The exemplary embodiments of the system and method proposed here for source separation can use the composite signal capture via different transducers not limited to accelerometer, acoustic, or piezoelectric. Any of these act as an electro-acoustic converter to establish a body sound for processing. The source separation provides the capability to extract signals while operating in a medium that is non-linear and time variant.

Figure 1A:
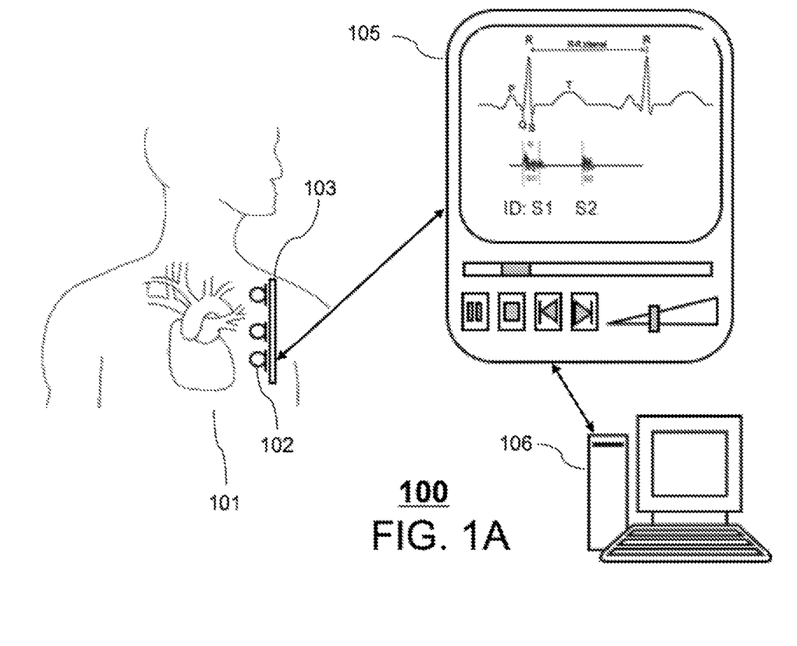
FIG. 1A illustrates a system for the source separation of the cardiopulmonary signals in accordance with one embodiment.
Figure 1B:
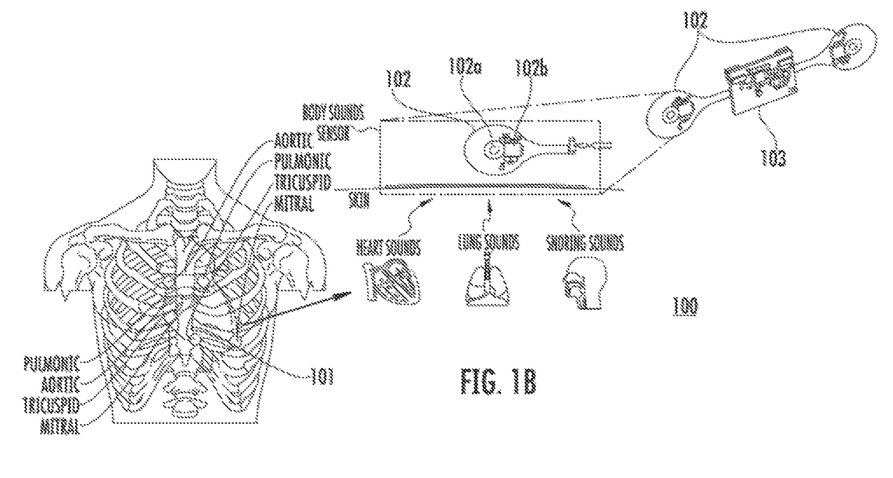
FIGS. 1B and 1C illustrate cardio pulmonary signal capture at the chest in accordance with various embodiments.
Figure 1C:
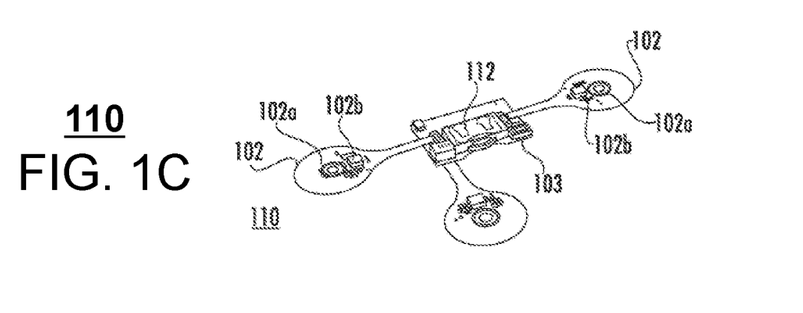

The exemplary embodiments of the system and method proposed here are shown in FIGS. 1A, 1B, and 1C. A system 100 is an embedded platform which can be any smart processing platform with digital signal processing capabilities, application processor, data storage, display, input modality like touch-screen or keypad, microphones, speaker, Bluetooth, and connection to the internet via WAN, Wi-Fi, Ethernet or USB or other wireless or wired connection. This embodies custom embedded hardware, smartphone, iPad-like and iPod-like devices. Area 101 in FIGS. 1A and 1B represents the auditory scene at the chest locations. A transducer array 102 captures the heart signal. In some embodiments, the transducer array 102 includes vibration sensors such as accelerometers. In some embodiments, the transducer array includes a pad that includes a vibration sensor such as a vibration sensor 102$b$ and an electrode 102$a$ for an ECG sensor. In some embodiments, the transducer array can include a single pad, two pads as shown in FIG. 1B or more than two pads as shown in FIG. 1C. In the particular embodiment of FIG. 1C, a transducer array 110 includes three pads (102) where each pad includes the vibration sensor 102b and the ECG electronic 102a. Other embodiments can include three or more pads where each pad would have at least a vibration sensor and optionally an electrode for the ECG sensor.

A wearable microprocessor hardware module 103 can include digital signal processing capabilities, application processor, Analog to digital frontend, data storage, input modality like buttons, wired connection or wireless connection via Bluetooth, Bluetooth low energy, near field communication transceiver, Wi-Fi, Ethernet or USB. The module 103 can include the signal processing module on the wearable hardware module 103 that captures synchronized sensor data from the transducer array 102. The module saves the captured synchronized sensor data to memory (locally or elsewhere) and communicates with the system 100 for data transfer. A module 105 communicatively coupled to the module 103 can calculate vital signs from the input sensor stream coming from the module 103 for the Heart rate, breathing rate, EKG signal, skin temperature, and associated vitals. The module 105 can encrypt the raw sensor data for transmission to a cloud computing module 106. The module 105 also communicates with a dashboard on 106 for data exchange, login, alerts, notifications, display of processed data. Module 106 in FIG. 1 serves as the cloud module that processes the individual streams for eventual source separation and optionally for identification and marking of the heart valve signals. In some embodiments, the system 100 in allows a user to visually see the individual streams and information of the different cardiopulmonary signals, and in some embodiments the system could present streams or information on a connected display or any other modality of display. The transducer array 102 can include multiple sensor transducers that capture the composite signal that includes the electrocardiogram signals, heart sounds, lung sounds and snoring sounds. The module 103 can be in the form of the wearable hardware that synchronously collects the signals across the transducers and is responsible for the analog to digital conversion, storage and transmission to a portable unit 105. Note that the embodiments herein are not limited to processing the individual streams for source separation, identification and marking of the heart valve signals at the cloud computing module 106 only. Given sufficient processing power, the aforementioned processing can occur at the microprocessor hardware module 103, at the module 105, or at the cloud-computing module 106, or such processing can be distributed among such modules 103, 105, or 106.

Figure 2:
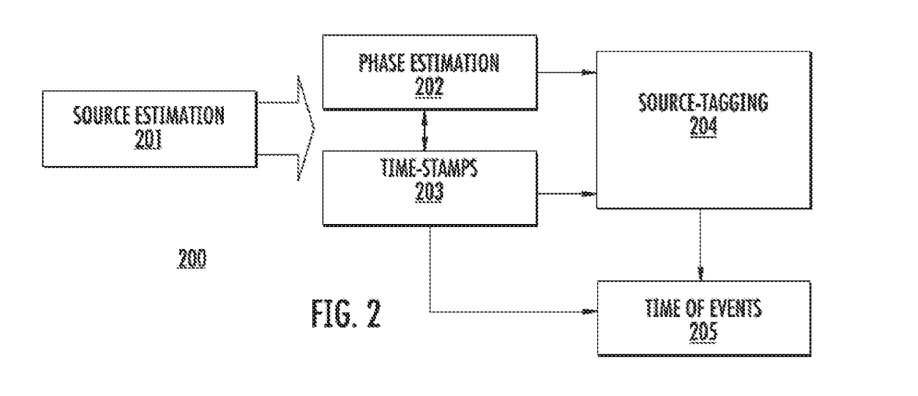
FIG. 2 is a flowchart of a method of Source-tagging practiced by the system in accordance with one embodiment.

In some embodiments, the system and method 200 as shown in FIG. 2 can include source extraction, identification and marking of the heart valve signals or cardiopulmonary signals. Block 201 indicates the separation of sources from the composite signals which can be done by source estimation using, for example, machine learning, auditory scene analysis, or sparse coding. Block 202 represents the phase estimation between the separated sources at each of the sensor positions. Block 203 represents calculating the time stamps of individual sources at each heartbeat with respect to the synchronized EKG signal and the other sensor or sensors. Block 204 represents the source identification module responsible for tagging each of the separated source in individual heart beats to be one of the heart valve event, namely the Mitral valve closing and opening, the Tricuspid valve closing and opening, the Aortic valve opening and closing, and the Pulmonic valve opening and closing. Block 205 represents the time marking module to estimate the time of occurrence of the above-mentioned valve events with respect to the start of the EKG signal.

Figure 3:
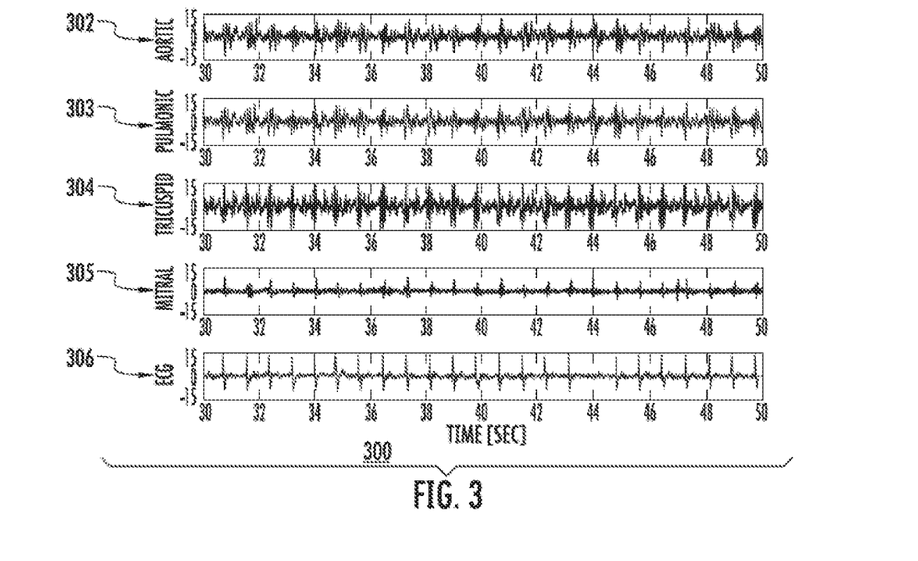
FIG. 3 illustrates Individual streams from the sensors on the wearable microprocessor in accordance with one embodiment.

The exemplary embodiments of the system and method proposed here for the source extraction using source separation of the cardiopulmonary signals from the composite signal 300 are shown in FIG. 3. Area(s) 101 illustrated in FIG. 1 indicates the locations at which the composite heart signal can be captured. A vibration signal 302 as charted on the first line of FIG. 3 represents a vibration signal captured at the aortic auscultation location. A biration signal 303 represents a vibration signal captured at the pulmonic auscultation location. A vibration signal 304 represents a vibration signal captured at the tricuspid auscultation location. A vibration signal 305 represents a vibration signal captured at the mitral auscultation location. The last or bottom line in FIG. 3 represents an electrocardiogram signal captured. In some embodiments, note that the number of sensors used (such as in the sensor array 102 of FIG. 1), are less than the number of vibration sources. For example, 3 sensors can be used to ultimately extract signals for 4 (or more) vibration sources; or 2 sensors can be used to ultimately extract signals for 3 or 4 (or more) vibration sources; or 1 sensor can be used to ultimately extract signals for 2, or 3, or 4 (or more) vibration sources.

Figure 4:
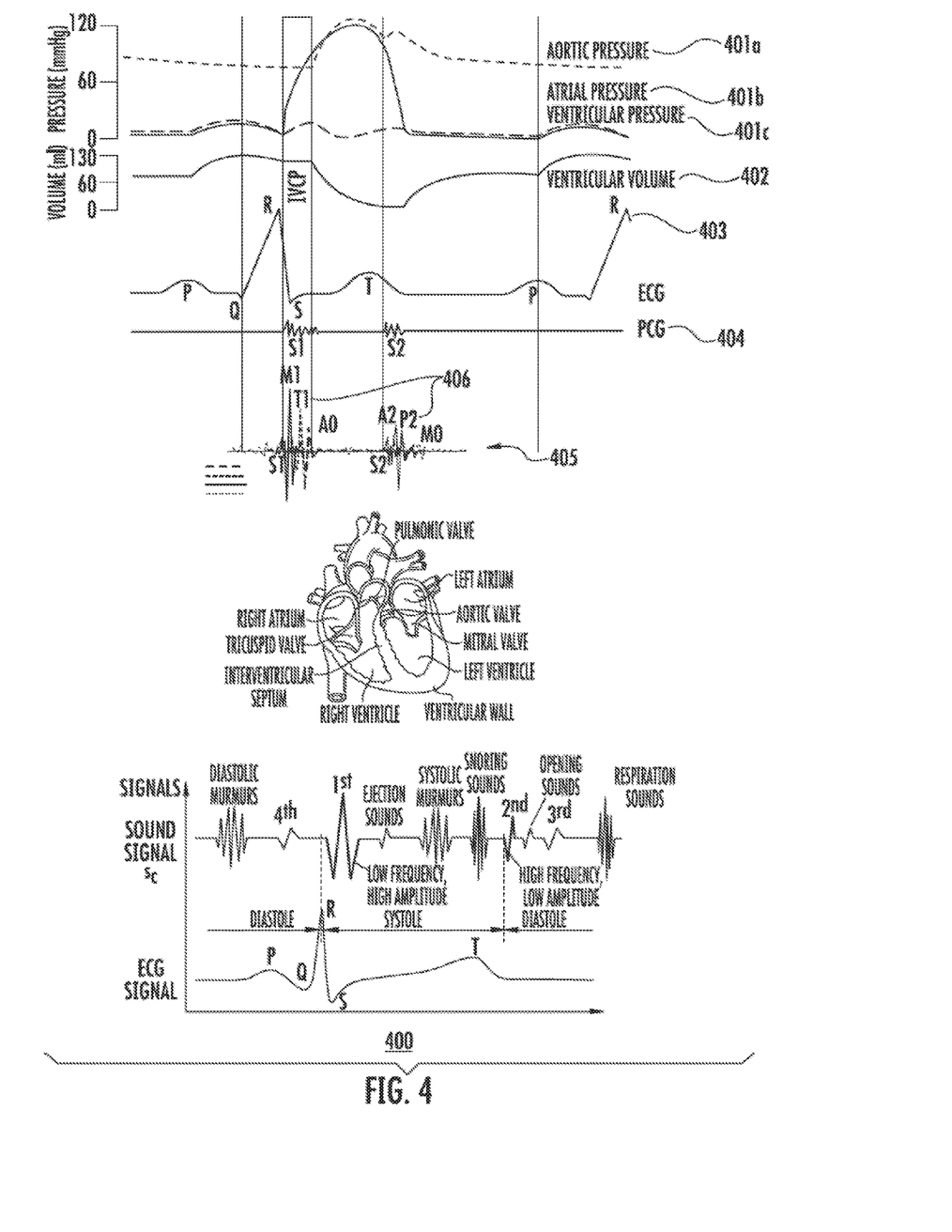
FIG. 4 illustrates a cardiac cycle in relation with Electrocardiogram, acoustic and accelerometer sensors of the system in accordance with one embodiment.

The exemplary embodiments of the system and method proposed here draw inspirations from biology with respect to the cardiac cycle in-relation with electrocardiogram and accelerometer transducer captured cardiac signal. A timeline chart 400 in FIG. 4 shows the cardiac cycle. Lines or signals 401a, 401b, and 401c represent or indicate the pressure changes during a cardiac cycle for aortic pressure (401a), atrial pressure (401b) and ventricular pressure (401c) measured in millimeters of mercury (mmHg). Line or signal 402 represents or indicates the volume changes during a cardiac cycle in milliliters (ml). Line or signal 403 represents or indicates the electrical changes during a cardiac cycle captured by an electrocardiogram. Line or signal 404 represents or indicates the acoustic changes during a cardiac cycle captured by an acoustic sensor such as a phonocardiogram or PCG. S1 represents the first heart sound or the "lub" sound and the S2 represents the second heart sound or "dub" sound. Line or signal 405 represents or indicates the vibration changes during a cardiac cycle captured by an accelerometer transducer at the location of the device. Pattern 406 indicates the different valve opening and closing seen in line or signal 405 as captured by the accelerometer sensor or sensors. More specifically, a closer inspection of the pattern 406 reveals the closing of the mitral valve (M1) and tricuspid valve (T1) during the S1 or first heart sound and the closing of the aortic valve (A2) and pulmonary valve (P2). The bottom half of FIG. 4 goes on to further show a representation of the anatomy of the human heart relevant for the generation of the sounds and a corresponding graph representing the sounds belonging to coronary artery, murmurs, first sound, second sound, third sound, fourth sound, ejection sounds, opening sounds, respiratory sound, breathing, and snoring during individual heart beats, with respect to the electrocardiogram signal. Briefly, during S1, blood flows in from the pulmonary veins and fills the left atrium and causes the mitral valve to temporarily (open and close) provide access to the left ventricle while almost simultaneously the blood from the superior vena cava fills the right atrium and causes the tricuspid valve to temporarily (open and close) provide access to the right ventricle. The left and right ventricles subsequently fill up with blood and during S2 the aortic valve and pulmonary valves each open and close in quick succession as blood is pumped towards the aorta and pulmonary artery respectively. The first heart sound (S1) when recorded by a high-resolution phonocardiography (PCG) can consist of 5 sequential components that first includes small low frequency vibrations, usually inaudible, that coincide with the beginning of left ventricular contraction, second, includes a large high-frequency vibration, easily audible related to mitral valve closure (M1), third, includes a second high frequency component closely following M1 and related to tricuspid valve closure T1, fourth, S1 includes small frequency vibrations that coincide with the acceleration of blood into the great vessel at the time of aortic valve opening A0, and fifth, S1 includes small frequency vibrations that coincide with the acceleration of blood into the great vessel at the time of pulmonic valve opening P0. The two major audible components are the louder M1 best heard at the apex followed by T1 heard best at the left lower sternal border. They are separated by only 20-30 ms and at the apex are only appreciated as a single sound in the normal subject as the aforementioned "Lub". The second heart sound (S2) have two major components A2 and the P2 are coincident with the incisura of the aorta and pulmonary artery pressure trace, respectively, and terminate the right and left ventricular ejection periods. Right ventricular ejection begins prior to left ventricular ejection, has a longer duration, and terminates after left ventricular ejection, resulting in P2 normally occurring after the A2 as shown in the pattern 406. The first high-frequency component of both A2 and P2 is coincident with the completion of closure of the aortic and pulmonary valve leaflets. As with sounds arising from the AV valves, A2 and P2 are not due to the clapping together of the valve leaflets but are produced by the sudden deceleration of retrograde flow of the blood column in the aorta and pulmonary artery when the elastic limits of the tensed leaflets are met. This abrupt deceleration of flow sets the cardio hemicsystem in vibration. The higher frequency components result in A2 and P2. Followed by the A2 and P2 are the vibrations associated with the valve openings. S2 includes small frequency vibrations that coincide with the acceleration of blood into the left ventrical at the time of mitral valve opening M0, and S2 includes small frequency vibrations that coincide with the acceleration of blood into the right ventrical at the time of tricuspid valve opening T0.

Figure 5A:
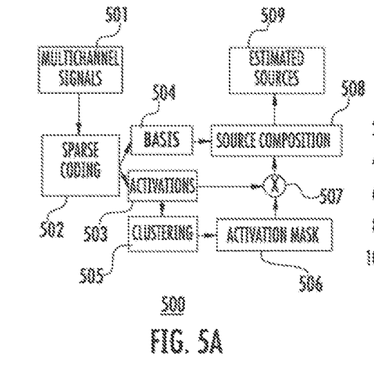
FIG. 5A illustrates the schematic of a source separation approach of extracting individual vibration objects or of each valve into individual streams in accordance with one embodiment.
Figure 5B:
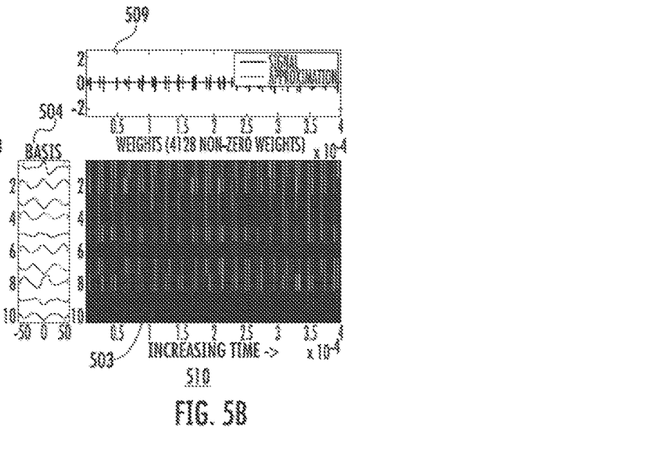
FIG. 5B illustrates graphic representations of the basis and activations used for the source separation approach of FIG. 5A in accordance with one embodiment.
Figure 5C:
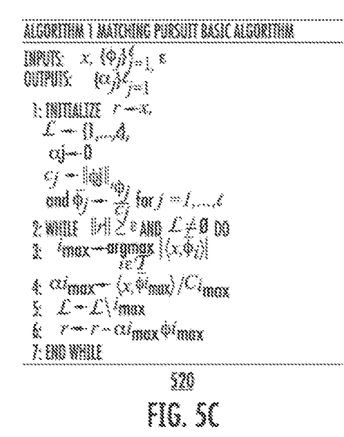
FIG. 5C shows a convolutional version of a matching pursuit algorithm to infer the activation of a given set of basis functions for use in the source separation approach of FIG. 5A in accordance with one embodiment.
Figure 5D:
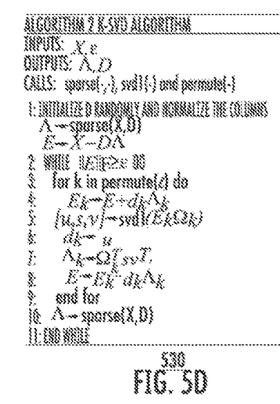
FIG. 5D shows a K-SVD algorithm to refine a set of basis elements given the desired signal and a set of activations for use in the source separation approach of FIG. 5A in accordance with one embodiment.
Figure 5E:
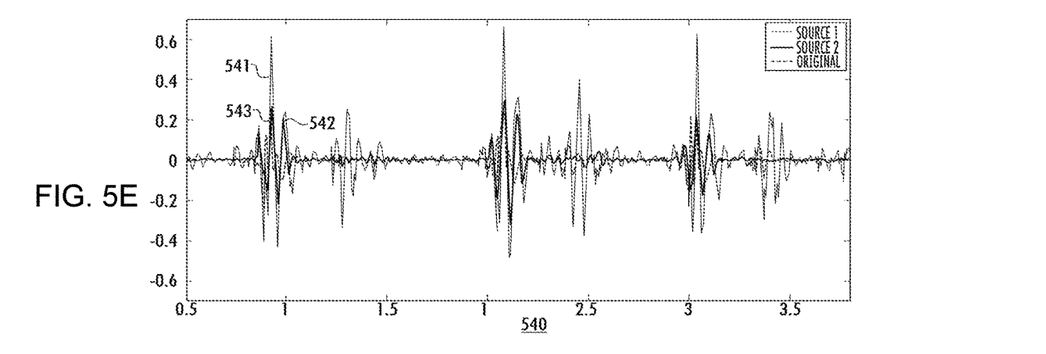
FIG. 5E illustrates the source separation using sparse coding in accordance with one embodiment.

The exemplary embodiments of the system and accompanying method proposed herein provide a source separation analysis algorithm that allows for the separation of the vibrations of the cardiopulmonary system as illustrated in the system 500 of FIG. 5A and corresponding chart cluster 510 of FIG. 5B. One of the proposed embodiments uses a separation algorithm based on sparse coding via a two stage process. First, the signals such as multichannel signals 501 are decomposed using sparse coding 502 into components that appear sparsely across a time chart 503 and further provide sparse activation patterns 504. Then, cluster analysis 505 on the sparse activation patterns 504 is performed. Time locations of activations patterns that are clustered together get assigned to the same source as shown in timeline 509. Finally, activations assigned to the same cluster using an activation mask 506 and a multiplier 507 are used along with the basis elements (504) to recompose the sources as the source composition 508. Estimated sources 509 can be determined or extracted from the source composition 508. Method 500 depicts the steps involved in the process. The boxes 502, 505, and 508 are considered computational modules and the boxes 501, 503, 504, 506, and 509 denote data which is either input or output to each module. In one implementation as shown in the algorithm 520 of FIG. 5C, a convolutional version of the matching pursuit algorithm to infer the activation of a given set of basis functions, and the K-means Singular Value Decomposition (K-SVD) algorithm 530 of FIG. 5D to refine a set of basis elements given the desired signal and a set of activations. In applied mathematics, K-SVD is a dictionary learning algorithm for creating a dictionary for sparse representations, via a singular value decomposition approach. K-SVD is a generalization of the k-means clustering method, and it works by iteratively alternating between sparse coding the input data based on the current dictionary, and updating the atoms in the dictionary to better fit the data. For clustering, employment of a k-means algorithm on a set of altered activation patterns can be used. The pseudo code for the matching pursuit algorithm is shown in algorithm 520 and the pseudo code for the KSVD is shown in algorithm 530. The techniques herein can employ time-based clustering of the basis activation patterns contained in the set of signals. There can be more than one source active within an analysis frame. The system 500 and corresponding chart 510 depicts the idea by showing two different activation patterns at two time instances that are assigned to different clusters. The resulting combination yields the separated signals as shown in chart 540 of FIG. 5E where the original signal is shown as 541, a first cluster is shown as 543 and a second cluster is shown as 542. Note, The embodiments can include different source separation techniques specifically used for extracting the valve heart signals for application in a non-linear time variant system, where the number of sensors is less than the number of sources.

Figure 6A:
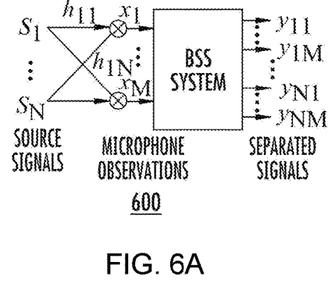
FIGS. 6A, 6B, and 6C illustrate the source separation using Bin-wise Clustering and Permutation posterior probability Alignment in accordance with one embodiment.
Figure 6B:
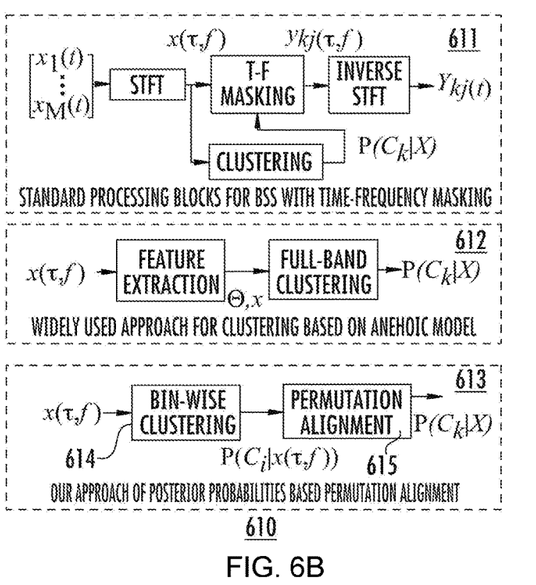
Figure 6C:
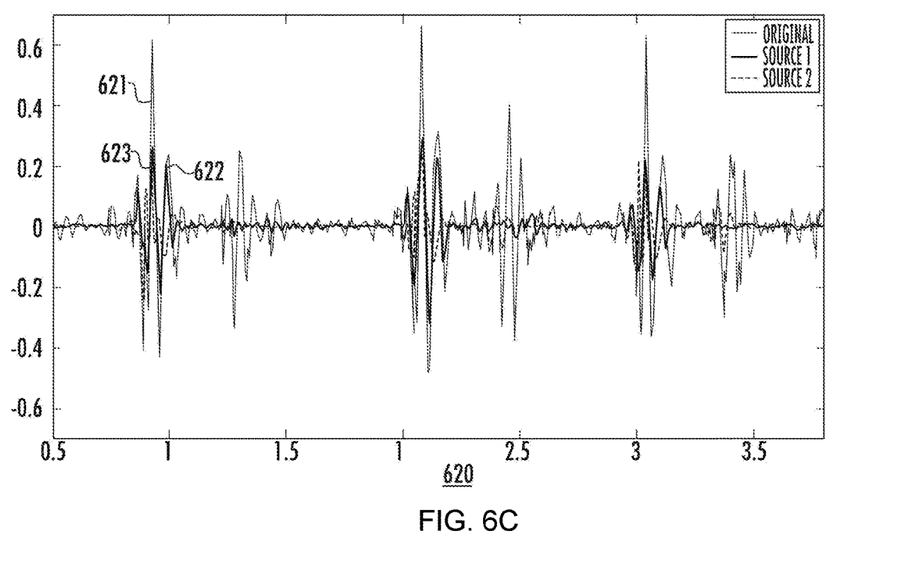

The exemplary embodiments of the system and method proposed here provide a source separation analysis algorithm that allows for the separation of the vibrations of the cardiopulmonary system using blind signal separation (BSS) or a BSS system. One of the proposed embodiments is a separation algorithm via Bin-wise Clustering and Permutation Alignment as shown in system 600 of FIG. 6A and one of the BSS options 610 of FIG. 6B. Although the optional techniques 611 and 612 can be used, the separation technique 613 using posterior probabilities provide a much clearer difference between same-source and different-source when calculating their correlation coefficients, as long as different sources are not synchronized. As a result, the permutation alignment capability provides considerable improvement over other methods. This innovation allows the separation of the cardiopulmonary sounds as shown in the system 600 and further illustrated in the chart 620 of FIG. 6C with the original signal 621, first separated source signal 622 and the second separated source signal 623 shown. The purpose of the two-stage structure in the separation technique 613 using the bin-wise clustering 614 and the permutation alignment 615 is to tackle the reverberation problem and handle non-linear-time-variant transfer mediums. The approach has no assumption as regards the mixture model. It can be adapted to various impulse responses, as long as the short time Fourier transform analysis window covers the main part of the impulse responses. After the first stage, we have posterior probabilities for all sources and all time-frequency slots. Next we determine a permutation to reorder the indices so the same index corresponds to the same source over all frequencies. Multiple centroids per source are used in the optimization. The fine local optimization is performed for one selected frequency at a time, and repeated until no improvement is found for any frequency. The source separated output is shown in the chart 620 of FIG. 6C.

Figure 7A:
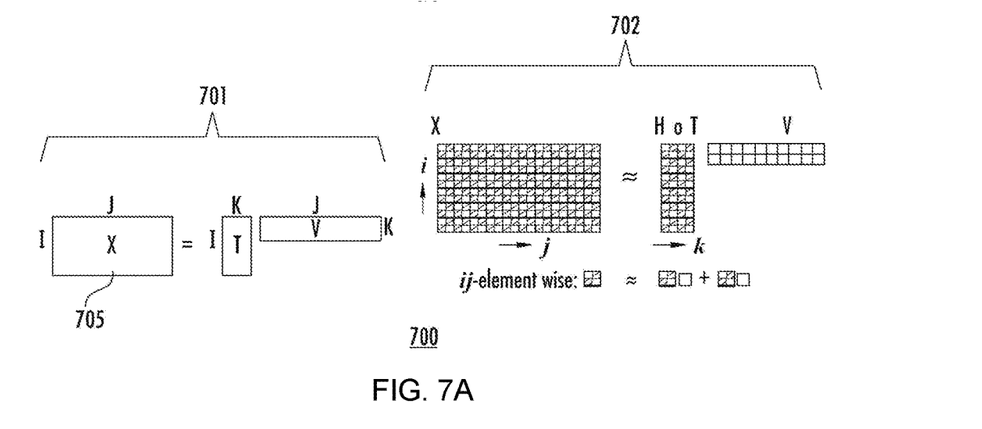
FIGS. 7A and 7B illustrate the source separation using Non-negative matrix factorization in accordance with one embodiment.
Figure 7B:
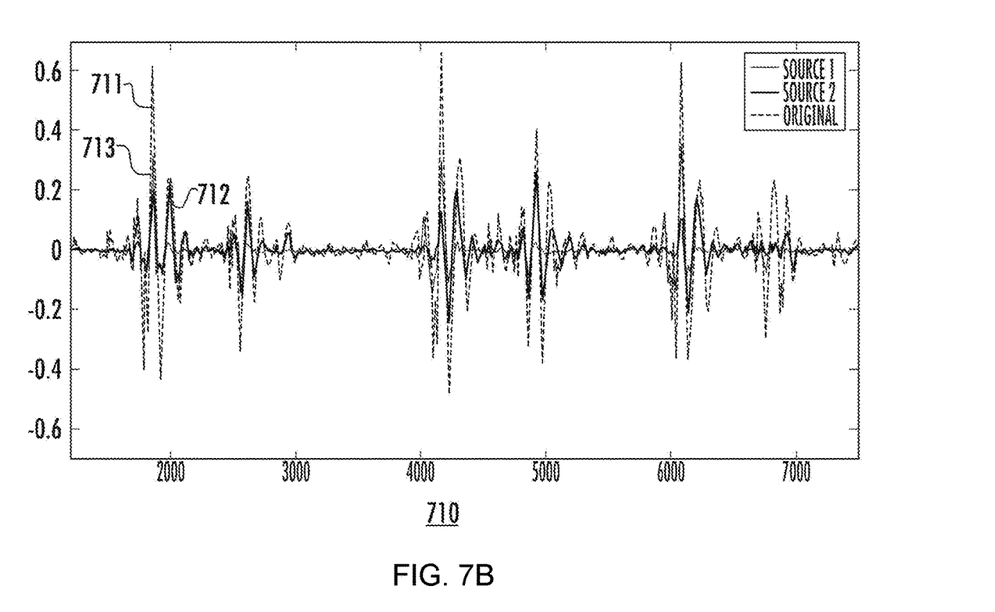

The exemplary embodiments of the system and method proposed herein provide a source separation analysis algorithm that allows for the separation of the vibrations of the cardiopulmonary system. One of the proposed embodiments is a separation algorithm via Non-negative matrix factorization based separation as represented by the algorithmic blocks 701 and 702 of system or method 700 of FIG. 7A. Multichannel extensions of Non-Negative Matrix Factorization (NMF) is an unsupervised learning technique. The NMF-based method generally performed better than existing methods that rely on the spatial property and simple time-wise activity information of each source. The method follows an idea similar to sparse coding, but additional constraints are imposed on the values to be approximated. The main idea is to factorize a nonnegative matrix A into the product TV of two nonnegative matrices, such that a notion of distance between X and TV is minimized. In practice the rank of TV can be controlled by the sizes of the factors matrix T and V. Namely, T is allowed to have k columns and thus V will have k rows. In this sense the product can be through as an encoding, where the columns of V can be interpreted as the coefficients of a scaled convex combination of the k columns of T. For example, in cardiopulmonary sounds X can be a time frequency distribution of magnitudes 705. To extend the above idea to multiple channels refer to block 702. The notion of nonnegative definiteness is employed as a natural extension of nonnegative numbers for squared matrices. Each one of the small blocks in X is of size M×M where M is the number of channels. The blocks in H can represent cross-correlations in frequency domain which can be interpreted as the phase differences between channels. To define the sources, H is further decomposed into convex combination of/matrices (sources). Separation results on the Tricuspid (acoustic channel) Complex Valued Multichannel extension of non-negative matrix factorization are shown in chart 710 of FIG. 7B.

Figure 8A:
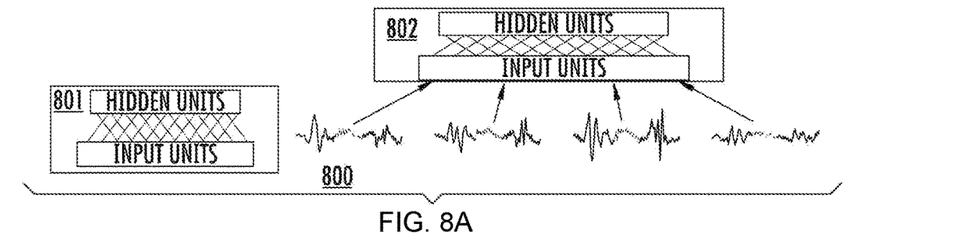
FIGS. 8A, 8B, 8C, and 8D illustrate the source separation using Deep Belief Networks in accordance with one embodiment.
Figure 8B:
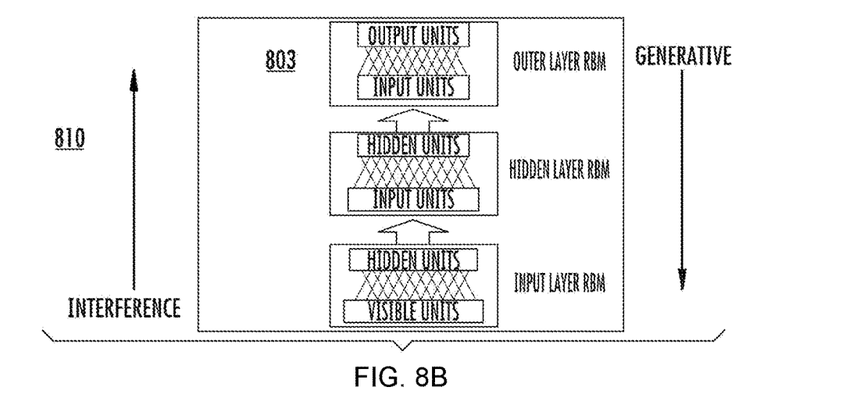
Figure 8C:
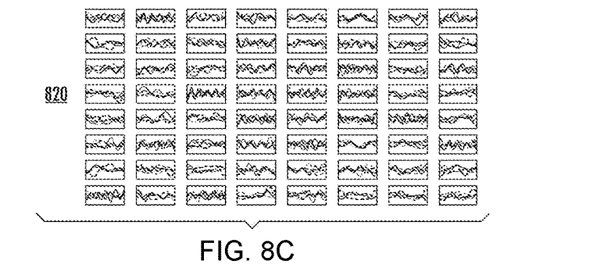
Figure 8D:
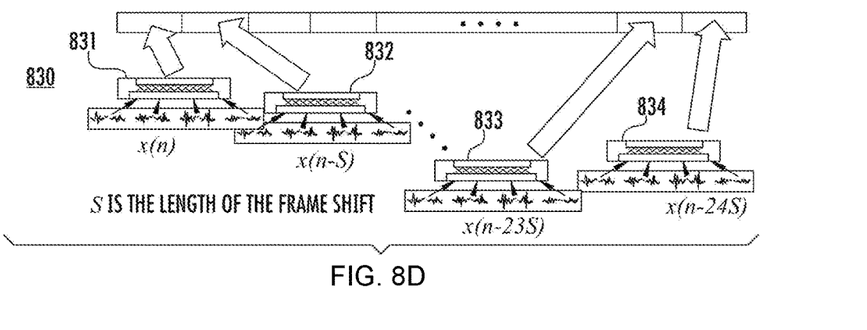

The exemplary embodiments of the system and method proposed here provide a source separation analysis algorithm that allows for the separation of the vibrations from the cardiopulmonary system. One of the proposed embodiments is a separation algorithm via Deep Belief Networks ("DBN" and also known as Restricted Boltzmann Machine) represented by the system 800 in FIG. 8A. Deep belief networks are probabilistic generative models composed of several hidden layers 801 and 802 of stochastic latent variables. The generative process in the flow chart 803 of system 810 of FIG. 8B works top down, whereas the inference process which predicts the values of the hidden variables given an input works bottom up. Deep belief networks are composed of stacked modules known as restricted Boltzmann machines (RBM)s. An RBM is a bipartite undirected graph with two sets of variables. A set of visible variables and a set of hidden variables. As the hidden layers 801 and 802 show, there are no connections among the visible and among the hidden variables. Only connections from visible to hidden variables and vice versa are allowed. In their most basic form, the RBM's visible and hidden variables are binary. The joint probability, of a given state of the RBM is defined through an energy function. A natural way to learn the parameters (connected weights) of this model based on a set of observations would be to maximize the log likelihood log p(v) of the observed variables. A gradient-based update of the log p(v) is used. Since the model probability distribution is not tractable, embodiments resort to an approximation of the expectation with respect to the model using a single step Gibbs sampling. This procedure is known as contrastive divergence and provides an efficient way to learn the model parameters. However, the price paid is that the log likelihood is no longer the objective. A more general type of RBM with units other than binary can be also constructed. Even in these cases, the contrastive divergence procedure to learn parameters remains essentially the same. Here, we will introduce an RBM architecture, which has no binary units, that can be employed to extract features from the raw multichannel recordings 820 shown in FIG. 8C. Stochastic gradient updates using contrastive divergence can be carried out in parallel. This procedure requires two types of operations: sampling operations and matrix operations. In this case all parameters are kept in global memory along with big batches of data samples that are rotated (replaced by another batch) every other number of iterations depending on the size of the batch. In the case of the sampling operations, at each parameter update, we perform random access of a subsample (minibatch) from the batch of samples that is currently loaded in global memory. Each block works on a single sample and a thread in the block works on a single dimension. This is possible, because of the conditional independence that arises from the bipartite graph restriction of the model. After we parallelize the training procedure of the DBN as shown in system 830 of FIG. 8D, at testing time we perform inference with the network of trained weights. For inference the DBN can be considered as feed forward neural net. The advantage with this choice is that inference can be performed with a simple forward pass with no iterative procedures. At a reasonable scale this can be ideal for a portable device were computational resources maybe limited. We use the RBM to represent signal frames of 128 msec. Each frame can be considered as a vector in $R^d$ where d corresponds to the number of samples that are obtained in 128 at a certain sampling frequency. Since we have c channels the dimensionality of the input vector is d. c each dimension is an input of the RBM. Therefore, we model the input units as Gaussian units. For the hidden units, we employ stepped sigmoid units (SSU). These units can be well approximated by noisy rectified linear units with activation of the form max(O,N(x, σ(x))). Where x is the argument of the activation function, σ(.) is the logistic sigmoidal function, and N(μ, $σ^2$) denotes a realization of a Gaussian random variable with mean μ and variance $σ^2$ (see 802). FIG. 8C shows the learned features for a set of multichannel recording 820 captured on the chest wall using the accelerometer transducers. The different colors of each line in recording 820 would depict the channel: for example, a blue line for aortic, green line for pulmonic, red line for tricuspid, and cyan line for mitral. The rectifier linear unit will promote sparseness of the representation since they will only become active is there a large correlation between the frame and the feature. FIG. 8D represents the feature extraction for multichannel heart signals using RBMs by creating a context frame 830. In this work, a context frame is the concatenation of the feature vectors 831, 832, 833, and 834) from frames that are consecutive in time. This concatenation creates a temporal context for the extracted features. We chose a context frame size of 25 frames with 50% overlap. This means each context frame covers 1600 milliseconds and therefore it is expected to contain at least one full heart beat. The RBM feature extractor contains 64 units for total of 1600 dimensions representing the context frame.

Figure 9A:
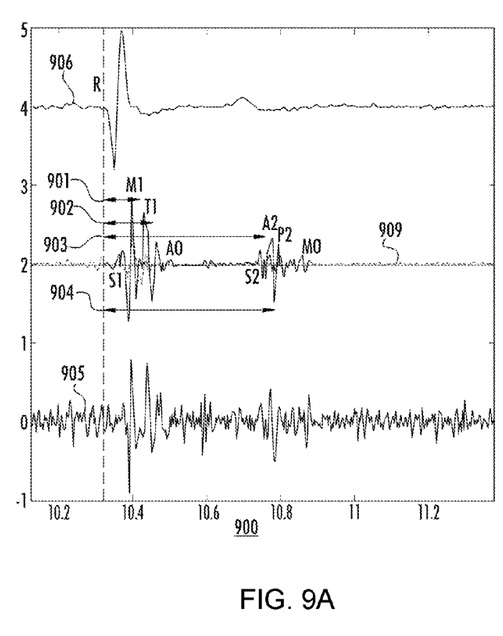
FIGS. 9A and 9B illustrate the source separation outputs in accordance with one embodiment.
Figure 9B:
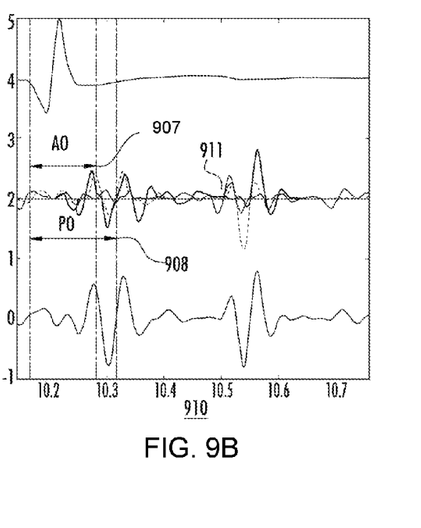

The exemplary embodiments of the system and method proposed here provide source separation algorithms that allow from the explanation earlier for the separation of cardiopulmonary signals. The charts 900 and 910 of FIGS. 9A and 9B respectively show the Mitral valve closing (MC), Mitral valve opening (MO), Aortic valve opening (AO), Aortic valve closing (AC), Tricuspid valve closing (TC), Tricuspid valve opening (TO), Pulmonary valve closing (PC) and Pulmonary valve opening (PO) signals. The extracted individual valve vibration objects are aligned into a signal for each of the four valves across multiple heart beats. FIGS. 9A and 9B show the source separation of heart valve opening and closing signals. Line 901 indicates the length or duration of the vibration signal for the Mitral valve closing (M1). Line 902 indicates the length or duration of the vibration signal for the Tricuspid valve closing (T1). Line 903 indicates the length or duration of the vibration signal for the Aortic valve closing (A2). Line 904 indicates the length or duration of the vibration signal for the Pulmonic valve closing (P2). Line 905 indicates the composite vibration signal captured by a particular transducer. Signal 906 indicates the EKG signal captured by the system. Referring to chart 910 of FIG. 9B, the Line 907 indicates the length or duration of the vibration of the Aortic valve opening (AO). Line 908 indicates the length or duration of the vibration of the Pulmonic valve opening (PO). Further note that the lines or signals 909 in FIG. 9A or 911 in FIG. 9B are actually several separated superimposed signals representing the vibration signals from separate sources coming from the mitral valve, tricuspid valve, aortic valve, and pulmonary valve (using less than 4 vibration sensors to extract such separated signals in some embodiments).

In the exemplary embodiments we develop various novel ways of source separating individual heart vibration events from the composite vibration objects captured via multiple transducers that can work on a single package that is embodied by an easy-to-use and portable device.

The exemplary embodiments develop novel methods of source separation, which in one embodiment lends the system capable of identifying individual cardiopulmonary events from the vibrations. The source separation (SS) algorithm work with arbitrarily arranged multiple sensors is capable of working with two or more transducers and that handles multiple sources in reverberant and noisy environments. The embodiments are capable of separating more sources than the number of transducers or microphones used (Underdetermined use-case). The system in accordance with some embodiments handles spatial aliasing and the algorithms are further able to separate signals in media that is non-linear, has time varying propagation, and heavily reverberant. The embodiments do not explicitly require sensor location information and can be arranged in any two or three dimensions' form.

The exemplary embodiments develop a novel method of source separation, which in one embodiment uses the Pulmonary and Aortic auscultation locations, and in addition possibly the Tricuspid and Mitral auscultation locations, lends the system capable of marking the time of occurrence of the individual valve events with respect to the electrocardiogram. The embodiments herein enable the system to measure the time intervals of the cardiopulmonary events.

The exemplary embodiments develop a novel method of providing source separation of individual signals over time. The novel method allows for both short-term and long-term discrimination between signals. Short-term pertains to tracking individual streams when they are captured simultaneously as part of the composite signal. Long-term tracking pertains to tracking individual streams across multiple heart beats, tracking valve signals as they transition in and out during each cardiac cycle.

The exemplary embodiment of system and method described is the development of an embedded hardware system, the main elements required to capture body sounds are the sensor unit that captures the body sounds, digitization, and digital processing of the body sounds for noise reduction, filtering and amplification. Of course, more complicated embodiments using the techniques described herein can use visual sensors, endoscopy cameras, ultrasound sensors, MRI, CT, PET, EEG and other scanning methods alone or in combination such that the monitoring techniques enable improvement in terms of source separation or identification, and/or marking of events such as heart valve openings, brain spikes, contractions, or even peristaltic movements or vibrations. Although the focus of the embodiments herein are for non-invasive applications, the techniques are not limited to such non-invasive monitoring. The techniques ultimately enable diagnosticians to better identify or associate or correlate detected vibrations or signaling with specific biological events (such as heart valve openings and closings, brain spikes, fetal signals, or pre-natal contractions.)

It will be apparent to those skilled in the art that various modifications may be made in the present invention without departing from the spirit or scope of the invention. Thus, it is intended that the present invention cover the modifications and variations of this invention provided they come within the scope of the method and system described and their equivalents.

What is claimed is:

1. A system for measuring cardiac time intervals, comprising:
   a non-invasive sensor unit for capturing electrical signals and composite vibration objects; and
   a processor for separating a plurality of individual heart vibration events from the composite vibration objects by using at least one among bin-wise clustering and permutation alignment, or non-negative matrix factorization, or deep belief networks; and
   wherein the processor is further configured for identifying the individual valve events from the plurality of individual heart vibration events with respect to an electrocardiogram signal for presenting the individual valve events superimposed with a synchronized electrocardiogram signal.

2. The system for measuring cardiac time intervals of claim 1, wherein the non-invasive sensor unit includes a first sensor configured for placement at or near a pulmonary auscultation location and a second sensor configured for placement at or near an aortic auscultation location.

3. The system for measuring cardiac time intervals of claim 1, wherein the non-invasive sensor unit includes a sensor configured for placement at or near a tricuspid auscultation location and a sensor configured for placement at or near a mitral auscultation location.

4. The system for measuring cardiac time intervals of claim 1, wherein the non-invasive sensor unit includes a first sensor configured for placement at a pulmonary auscultation location, a second sensor configured for placement at an aortic auscultation location, and at least a third sensor configured for placement at a tricuspid auscultation location or at a mitral auscultation locations or both.

5. The system for measuring cardiac time intervals of claim 1, further comprising a sensor for performing an electrocardiogram and wherein the non-invasive sensor unit comprises at least one sensor for sensing a heart valve opening.

6. The system of claim 1, wherein the permutation alignment is a posterior based permutation alignment.

7. The system of claim 1, wherein the deep belief networks uses stacked modules of restricted Boltzmann machines to create a context frame having a concatenation of feature vectors from frames that are consecutive in time.

8. The system for measuring cardiac time intervals of claim 1, wherein the processor is configured to separate the plurality of individual heart vibration events from the composite vibration objects from multichannel signals by decomposing the multichannel signals into sparse activation patterns and clustering the sparse activation patterns.

9. The system for measuring cardiac time intervals of claim 1, wherein the system comprises a wearable device in the form of a patch, band, necklace, belt, or bandage configured to communicate with a wireless node and further configured to capture an electrocardiogram signal synchronized with one or more accelerometer sensors of the non-invasive sensor unit.

10. The system for measuring cardiac time intervals of claim 1, wherein the non-invasive sensor unit comprises at least one sensor for sensing vibrations corresponding to a heart valve opening.

11. The system for measuring cardiac time intervals of claim 1, wherein a number of vibration sensors in the non-invasive sensor unit is less than a number of separated vibration sources coming from one or more of a mitral valve, a tricuspid valve, a aortic valve, and/or a pulmonary valve.

12. The system for measuring cardiac time intervals of claim 1, wherein the processor separates a plurality of individual heart vibration events from composite vibration objects from multichannel signals using at least one source separation technique used for extracting the valve heart signals for application in a non-linear time variant system, among Determined Models, Principal Component Analysis (PCA), Independent Component Analysis ICA, Singular Value Decomposition (SVD), Bin-wise Clustering and Permutation posterior probability Alignment, Undetermined Models, Sparseness condition, Dictionary learning, Convolutive models, or K-SVD Matching Pursuit.

13. The system for measuring cardiac time intervals of claim 1, wherein a marking of individual valve events comprises at least the marking of one or more among a Mitral valve opening (MO), Aortic valve opening (AO), Tricuspid valve opening (TO), or Pulmonary valve opening (PO).

14. A sensor array device, comprising:
at least one accelerometer;
a wearable device configured to capture an electrocardiogram signal synchronized with composite vibration objects from the at least one accelerometer and further configured to communicate with a wireless node;
wherein the at least one accelerometer is configured for capturing the composite vibration objects;
an electrode for sensing the electrocardiogram signal; and
a processor for separating a plurality of individual heart vibration events from the composite vibration objects by using at least one among bin-wise clustering and permutation alignment, or non-negative matrix factorization, or deep belief networks.

15. The sensor array device of claim 14, wherein the at least one accelerometer are configurable for measuring a lower frequency range vibration signal and a higher frequency range vibration signal.

16. The sensor array device of claim 14, wherein the processor is operatively coupled to the at least one accelerometer, the processor further being configured for:
identifying the plurality of individual heart vibration events from the composite vibration objects;
transmitting the composite vibration objects or the plurality of individual heart vibration events to a remote device; and
marking and presenting individual valve events from the plurality of individual heart vibration events with respect to the electrocardiogram signal.

17. The sensor array device of claim 14, wherein the at least one accelerometer comprises a first sensor configured for placement at or near a pulmonary auscultation location, a second sensor configured for placement at or near an aortic auscultation location, and at least a third sensor configured for placement at or near a tricuspid auscultation location or at or near a mitral auscultation location or both.

18. The sensor array device of claim 14, wherein the sensor array device is portable and captures synchronized sensor data to a memory and wherein the processor is configurable in the process of separating the plurality of individual heart vibration events from the composite vibration objects into separate vibration sources and further identifying the individual heart vibration events among at least one of a mitral valve opening, a tricuspid valve opening, an aortic valve opening, or a pulmonary valve opening.

19. The sensor array device of claim 14, further comprising a wireless connection for transmission of sensor data or processed sensor data to a remote computing device or a cloud computing device.

20. A system of measuring cardiac time intervals, comprising:
a memory having computer instructions; and
one or more processors operatively coupled to the memory, the execution of the computer instructions causing the one or more processors to perform operations comprising:
capturing composite vibration objects using a non-invasive sensor unit;
separating, by the one or more processors, a plurality of individual heart vibration events from the composite vibration objects using at least one among bin-wise clustering and permutation alignment, or non-negative matrix factorization, or deep belief networks;
identifying, by the one or more processors, the individual valve events from the plurality of individual heart vibration events with respect to an electrocardiogram signal, wherein the individual valve events comprises at least one among a mitral valve opening, a tricuspid valve opening, an aortic valve opening, or a pulmonary valve opening; and
presenting the individual valve events superimposed with a synchronized electrocardiogram signal.

* * * * *